US012729403B2

(12) United States Patent
Olek et al.

(10) Patent No.: US 12,729,403 B2
(45) Date of Patent: Sep. 8, 2026

(54) MYH11/NDE1 REGION AS EPIGENETIC MARKER FOR THE IDENTIFICATION OF ENDOTHELIAL PROGENITOR CELLS (EPCs)

(71) Applicant: PRECISION FOR MEDICINE GMBH, Berlin (DE)

(72) Inventors: Sven Olek, Berlin (DE); Kati Bourquain, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 882 days.

(21) Appl. No.: 17/997,163

(22) PCT Filed: Apr. 26, 2021

(86) PCT No.: PCT/EP2021/060855

§ 371 (c)(1),
(2) Date: Oct. 26, 2022

(87) PCT Pub. No.: WO2021/219561

PCT Pub. Date: Nov. 4, 2021

(65) Prior Publication Data

US 2023/0265507 A1 Aug. 24, 2023

(30) Foreign Application Priority Data

Apr. 27, 2020 (DE) ..................... 10 2020 111 423.0

(51) Int. Cl.
*C12Q 1/68* (2018.01)
*C12Q 1/6881* (2018.01)

(52) U.S. Cl.
CPC ..... *C12Q 1/6881* (2013.01); *C12Q 2600/154* (2013.01)

(58) Field of Classification Search
None
See application file for complete search history.

(56) References Cited

U.S. PATENT DOCUMENTS 7,666,393 B2 2/2010 Soker et al.
2006/0035290 A1 2/2006 Popa et al.

FOREIGN PATENT DOCUMENTS

WO 2004001016 A2 12/2003
WO 2011/073521 A1 6/2011

OTHER PUBLICATIONS

Yu et al. (World Neurosurg. (2017) 105:28-36) (Year: 2017).*
Infinium HumanMethylation450 BeadChip Product information sheet, 2011, 2 pages (Year: 2011).*
Illumina Infinium HD Assay Methylation Protocol guide, 244 pages (Year: 2015).*
GenBank GU143399 (Dec. 7, 2009, *Homo sapiens* myosin, heavy chain 11, smooth muscle isoform 1 (MYH11) gene; 52 pages) (Year: 2009) Document in 2 PDF.*
Brodowski et al. (2019) Preeclampsia-Associated Alteration of DNA Methylation in Fetal Endothelial Progenitor Cells. Front. Cell Dev. Biol. 7:32. doi: 10.3389/fcell.2019.00032 (Year: 2019).*
Written Opinion of the International Searching Authority and International Search Report for International Patent Application No. PCT/EP2021/060855, mailed Aug. 16, 2021.
Human Chromosome 1 SNP PCR Primer, EBI Database Accession No. ADH27987, Mar. 11, 2004.
Brodowski et al., "Preexlampsia-Associated Alteration of DANN Methylation in Fetal Endothelial Progenitor Cells", Front Cell Dev. Biol., Mar. 2019, vol. 7, Article 32, pp. 1-14.

* cited by examiner

*Primary Examiner* — Juliet C Switzer
(74) *Attorney, Agent, or Firm* — BakerHostetler

(57) ABSTRACT

The present invention relates to a method, in particular an in vitro method, for identifying endothelial progenitor cells (EPCs), comprising analyzing epigenetic modifications/properties of (including the methylation status) of at least one CpG position in the mammalian gene region for muscle myosin heavy chain 11 (MYH11) and nuclear distribution protein nudE homolog 1 (NDE1), wherein a demethylation or lack of methylation of said gene regions is indicative for an EPC, when compared to a non-EPC. The analysis according to the invention can identify EPCs on an epigenetic level and distinguish them from all other cells in complex samples, such as, for example, other blood, non-blood or immune cells. The present invention furthermore provides an improved method for quantifying EPCs, in particular in complex samples. The method can be performed without a step of purifying and/or enriching cells, preferably in whole blood and/or non-trypsinized tissue.

11 Claims, 3 Drawing Sheets

Specification includes a Sequence Listing.

gcgccattgcactccagagcgagactccgtctcaaaaaaaaaaaaaaaaaaaagcaaaatcccagagcagcagagacctcttcatgctttcttgggaagggccctgtg
tgcatccttgagtcttgggtatccactccccagtccctgaacatgtacatgcccgtgaagcctccagaaaggctctgccaggactgtgcttggctttgcggtggtca
gcttccaccccgtgtgctgaaaatgcagtttgtagctagacatcactcaagccacgtgcagcccccggcatttgtcagacatcgcagtgagctcatttccttcgcaga
caagcctgtgaaagctgaatcatgggaggactggttgccgcgccgcagttaccgtgaactttgtgatctctgacttgtgacccagaccagccaactagaagccaagta
cgttctccaggaatgtgcccagatagtggaactgtcatattcattcagtgcagtgtcttcactggacaagggaggacagcactgctgagtgccctaaccacgtaagag
tggcttttggcatgaaaggaagaaaaatccaagctacacacacagcctctgccatctcgtcaagatgcagtgataagggcgcacactgttgggtgtcatgtcacatgt
gctgcccagaggcaggaaggacagtgggtcaagagatgaggtctatttgtcatcctgatcttggtttcaatgaaagctttgcacaaagatatccaagcctccagattt
tgcaagaatctcgtggaaatgtgcaagggtttaaaaattggggtgggcagaggggcgcattgggcagaaaagaaatggatactgagacaacacacagctgcgaagctg
aaggcatgatacctggtgcatcactgcgaagtttcctgtgggggggccctctgaaacagagagagaatccccggaggttaccatcagcaaacaagaaggagcccggt
taagtatattcttaattgttaaagacatttgcttcgatttaataattaaaggcactctttttttattttgagatagtctctgtcacccaggctggagtgcaggggtgcg
atc

FIG. 2

GAAGGGCCCT GTGTGCATCC TTGAGTCTTG GGTATCCACT CCCCAGTCCC TGAACATGTA CATGCCCGTG AAGCCTCCAG AAAAGGCTCT
GCCAGGACTG TGCTTGGCTT TGCGGTGGTC AGCTTCCACC CCGTGTGCTG AAAATGCAGT TTGTAGCTAG ACATCACTCA AGCCACGTGC
AGCCCCCGGC ATTTGTCAGA CATCGCAGTG AGCTCATTTC CTTCGCAGAC AAGCCTGTGA AAGCTGAATC ATGGGAGGAC TGGTTGCCGC
GCCGCAGTTA CCGTGAACTT TGTGATCTCT GACTTGTGAC CCAGACCAGC CAACTAGAAG CCAAGTACGT TCTCCAGGAA TGTGCCCAGA
TAGTGGAACT GTCATATTCA TTCAGTGCAG TGTCTTCACT GGACAAGGGA GGACAGCACT GCTGAGTGCC CTAACCACGT AAGAGTGGCT
TTTGGCATGA AAGGAAGAAA AATC

FIG. 3

MYH11/NDE1 REGION AS EPIGENETIC MARKER FOR THE IDENTIFICATION OF ENDOTHELIAL PROGENITOR CELLS (EPCs)

CROSS-REFERENCE TO RELATED APPLICATIONS

This application is the National Stage Application of International Patent Application No. PCT/EP2021/060855, filed on Apr. 26, 2021, which claims the benefit of German Patent Application No. DE 10 2020 111 423.0, filed on Apr. 27, 2020, which are hereby incorporated by reference in their entirety.

SEQUENCE LISTING

The instant application contains a Sequence Listing which is being submitted herewith electronically in ASCII format and is hereby incorporated by reference in its entirety. Said ASCII copy, created on-Apr. 8, 2023, is named 113828_000030_Sequence_Listing_2.txt and is 4,124 bytes in size.

The present invention relates to a method, in particular an in vitro method, for identifying endothelial progenitor cells (EPCs), comprising analyzing epigenetic modifications/properties of (including the methylation status) of at least one CpG position in the mammalian gene region for muscle myosin heavy chain 11 (MYH11) and nuclear distribution protein nudE homolog 1 (NDE1), wherein a demethylation or lack of methylation of said gene regions is indicative for an EPC, when compared to a non-EPC. The analysis according to the invention can identify EPCs on an epigenetic level and distinguish them from all other cells in complex samples, such as, for example, other blood, non-blood or immune cells. The present invention furthermore provides an improved method for quantifying EPCs, in particular in complex samples. The method can be performed without a step of purifying and/or enriching cells, preferably in whole blood and/or non-trypsinized tissue.

Furthermore, the present invention relates to a kit for performing the above methods as well as respective uses thereof. It is one aim of this invention to provide a novel, more robust means to quantitatively detect and measure EPCs of the blood within any solid organs, tissue or body fluid of a mammal, in particular cord blood.

BACKGROUND OF THE INVENTION

Human endothelial progenitor cells (EPCs) play an important role in regenerative medicine and contribute to neovascularization on vessel injury. They are usually enriched from peripheral blood, cord blood and bone marrow.

Nevertheless, the term EPC has been applied to multiple different cell types that play roles in the regeneration of the endothelial lining of blood vessels. EPCs have variable phenotypic markers used for identification, and unfortunately there are no unique markers for endothelial progenitors that are not shared with other endothelial or hematopoietic cells, which has contributed to the historical controversy surrounding the field.

Endothelial progenitor cells are likely important in tumor growth and are thought to be critical for metastasis and the angiogenesis. Higher levels of circulating "endothelial progenitor cells" were detected in the bloodstream of patients, predicted better outcomes, and patients experienced fewer repeat heart attacks. Further prospective functions are in would healing and endometriosis.

Brodowski et al. (in: Preeclampsia-Associated Alteration of DNA Methylation in Fetal Endothelial Progenitor Cells. Front Cell Dev Biol. 2019 Mar. 19; 7:32) show a diminished function of fetal endothelial colony-forming cells (ECFC), a proliferative subgroup of endothelial progenitor cells (EPC) in preeclampsia. They further investigated whether DNA methylation of fetal EPC is affected in preeclampsia, and a differential methylation pattern of fetal ECFC from preeclampsia compared to uncomplicated pregnancy was detected for a total of 1266 CpG sites in passage 3, and for 2362 sites in passage 5. Key features of primary networks implicated by methylation differences included cell metabolism, cell cycle and transcription and, more specifically, genes involved in cell-cell interaction and Wnt signaling. We identified an overlap between differentially regulated pathways in preeclampsia and cardiovascular system development and function.

Wang et al. (in: MeCP2-mediated epigenetic regulation in senescent endothelial progenitor cells. Stem Cell Res Ther. 2018 Apr. 3; 9(1):87) show Methyl-CpG-binding protein 2 (MeCP2) mediated senescent EPCs dysfunction through epigenetic regulation.

Hájková et al. (in: CBFB-MYH11 hypomethylation signature and PBX3 differential methylation revealed by targeted bisulfite sequencing in patients with acute myeloid leukemia J Hematol Oncol. 2014 Sep. 30; 7:66) disclose a hypomethylation pattern, specific to CBFB-MYH11 fusion resulting from inv(16) rearrangement that is associated with genes previously described as upregulated in inv(16) AML. Further, PBX3 differential methylation was found to correlate with its gene expression.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfite sequencing to map and quantify 5hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

WO 2012/162660 describes methods using DNA methylation arrays are provided for identifying a cell or mixture of cells and for quantification of alterations in distribution of cells in blood or in tissues, and for diagnosing, prognosing and treating disease conditions, particularly cancer. The methods use fresh and archival samples.

US 2003-0143606 discloses a nucleic acid comprising an at a least 18 bases-long sequence segment of the chemically pretreated DNA of 2420 genes associated with the immune system including the gene MYH11 (NM002474).

In view of the above, it is an object of the present invention to provide an improved and in particular specific and robust method based on DNA-methylation analysis as a superior tool in order to more conveniently and reliably detect, identify, discriminate, and quantify endothelial progenitor cells.

The present invention solves the above object by providing a method for identifying endothelial progenitor cells (EPCs) in a sample, comprising analyzing the methylation status (bisulfite convertibility) of at least one CpG position in the mammalian (e.g. human) gene region for muscle myosin heavy chain 11/nuclear distribution protein nudE homolog 1 (MYH11/NDE1) according to SEQ ID No. 1, wherein preferably said gene region as analyzed is positioned based on/according to SEQ ID No. 2, wherein a demethylation or lack of methylation of said gene region is indicative for an EPC, when compared to a non-EPC.

Myosin Heavy Chain 11 is a component of smooth muscle myosin belonging to the myosin heavy chain family and is encoded by the MYH11 gene. The gene NDE1 encodes the nudE neurodevelopment protein 1, a human ortholog of rat NUDE1. The two genes MYH11 and NDE1 are transcribed in opposite directions and overlap with their 3'-end. The pericentric inversion of chromosome 16 [inv(16)(p13q22)] produces a chimeric transcript that encodes a protein consisting of the first 165 residues from the N terminus of core-binding factor beta in a fusion with the C-terminal portion of the smooth muscle myosin heavy chain, and is associated with acute myeloid leukemia of the M4Eo subtype (Liu P P et al. Identification of the chimeric protein product of the CBFB-MYH11 fusion gene in inv(16) leukemia cells. Genes Chromosomes Cancer. 1996 June; 16(2): 77-87). Alternative splicing generates isoforms that are differentially expressed, with ratios changing during muscle cell maturation. Alternatively spliced transcript variants encoding different isoforms have been identified.

NDE1 is a member of the nuclear distribution E (NudE) family of proteins. The protein is localized at the centrosome and interacts with other centrosome components as part of a multiprotein complex that regulates dynein function. This protein plays an essential role in microtubule organization, mitosis and neuronal migration. Mutations in this gene cause lissencephaly 4, a disorder characterized by lissencephaly, severe brain atrophy, microcephaly, and severe cognitive disability. Alternative splicing results in multiple transcript variants.

There a quite a few genes in the human genome that structurally overlap, e.g. in the present case of the counter-strand-arranged genes for MYH11 (about 154 kb in size and 38 exons) and NDE1 (about 83 kb in size, 10 exons) whose 3'-ends overlap for about 24 kb. The present amplicon AMP3968 in both genes maps close the last intron, respectively. Therefore, the region presumably is functionally associated with both genes, with a probable slight preference to MYH11, because of the smooth muscle involvement thereof.

In the context of the present invention, the gene region shall comprise all of the genomic regions relating to and encoding for MYH11/NDE1. Thus, included are enhancer regions, promoter region(s), introns, exons, and non-coding regions (5'- and/or 3'-regions) that belong to MYH11 and/or NDE1. Preferred is thus a method according to the present invention, wherein the at least one CpG position is present in the 5' region upstream from the transcription start, promoter region, the 5' or 3' untranslated regions, exon, intron, exon/intron border and/or in the 3' region downstream of the transcriptional stop of the gene as analyzed.

The present invention is further based on the surprising identification of a regions of the MYH11/NDE1 genes by the inventors, as specific epigenetic marker, allowing the identification of EPCs as well as the clinical routine application of said analysis.

In the context of the present invention, the genomic region for muscle myosin heavy chain 11/nuclear distribution protein nudE homolog 1 (MYH11/NDE1) according to SEQ ID No. 1, in particular according to SEQ ID No. 2 (Amp 3968), allows for the identification of EPCs. Surprisingly, the discriminatory pattern of bisulfite convertible and non-convertible cytosine is particularly and even exclusively limited to the genomic region according to SEQ ID No. 1 for EPCs as shown using the amplicon according to SEQ ID No. 2.

The inventors could demonstrate that in the EPCs the CpG motifs as disclosed are almost completely demethylated (i.e. to more than 70%, preferably 80%, preferably, more than 90% and most preferred more than 95%), whereas the same motifs are nearly completely, and preferably completely methylated in non-EPCs.

The differential methylation of the CpG motifs within the aforementioned regions is a valuable tool to identify EPCs, such as will be required/or at least of some value for identifying and quantifying said cells in autoimmune diseases, transplant rejections, infection diseases, cancer, allergy, endometriosis, cardiovascular diseases, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context. The assay allows measurement of EPCs without purification or any staining procedures.

Another preferred aspect of the method according to the present invention then further comprises a quantification of the relative amount of EPCs based on comparing relative amounts of said methylation frequency in the region as analyzed with relative amounts of the methylation frequency in a control gene, such as, for example, GAPDH. Said quantification is thus achieved based on the ratio of the bisulfite convertible DNA to non-convertible DNA in the genetic region for muscle myosin heavy chain 11/nuclear distribution protein nudE homolog 1 (MYH11/NDE1) (e.g. of SEQ ID No. 1) as described and analyzed herein. Most preferred is a quantification of the relative amount of EPCs is based on an (preferably parallel or simultaneous) analysis of the relative amount of bisulfite convertible DNA of the cell-specific region for MYH11/NDE1, and of the relative amount of bisulfite convertible DNA of cell-unspecific genes (preferably designated "control genes" or "control regions", such as, for example, the gene for GAPDH).

In a further preferred embodiment of the method according to the present invention, said analysis of bisulfite convertibility comprises amplification with at least one primer of suitable primer pairs that can be suitably designed based on SEQ ID No. 1 or 2, preferably oligomers according to any of SEQ ID No. 3 to 12.

In contrast to flow cytometry and mRNA measurements, using the methods according to the present invention, the measurement(s) and analyses can be done independent of purification, storage—and to quite some extent—also to tissue quality.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, an amplicon of the MYH11/NDE1 gene region is produced that is a particularly preferred "tool" for performing the method(s) according to the present invention. Consequently, oligomers according to any of SEQ ID No. 3 to 12 or an amplicon as amplified by a primer pair based on SEQ ID No. 3 and 4 or 5 and 6 or 8 and 6 or 10 and 11 as mentioned herein constitute preferred embodiments of the present invention. Thus, the sequences of SEQ ID No. 1 to 2 (and, if needed, the complementary sequences thereto) can be used to design primers for amplifications, i.e. serve as "beacons" in the sequence as relevant. Similarly, additional primers and probes can be designed based on the amplicon according to SEQ ID No. 2. Amplification can take place either in the genomic and/or bisulfite (i.e. "converted") DNA sequence.

The person of skill will furthermore be able to select specific subsets of CpG positions in order to minimize the amount of sites to be analyzed, for example at least one of CpG position selected from a CpG position in an amplicon according to SEQ ID No. 1, and is preferably selected from the CpG positions 67, 113, 132, 176, 187, 204, 224, 268, 270, 273 and 282, optionally with 338 and 437 in the amplicon AMP 3968 according to SEQ ID No. 2, and is more preferably selected from CpG positions 67, 113, 132, 187, 204, 224, 268, 270, and 273 or CpG positions 67, 113, 204, 224, 268, 270, and 273, both optionally with 338 and 437 in a fragment of the amplicon AMP 3968 according to SEQ ID No. 2. Preferred are combinations of CpG positions 67, 113, 132, 187, 204, 224, 268, 270, and 273 for distinguishing EPCs from blood cells. Preferred are combinations of 3, 4, 5, 6, 7, 8, 9, 10, 11, 12 or 13 positions, the analysis of which produces sufficient data and/or information in order to be informative in the context of the present invention.

In order to analyze the bisulfate convertibility of CpG positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. These methods are well known to the person of skill, and can be found in the respective literature.

In a preferred embodiment of the method according to the present invention, said method is suitable for routine application, for example on a DNA—such as an oligonucleotide-based chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said EPCs from all major peripheral blood cell types and/or non-blood cells, or cord blood cells, preferably, but not limited to, CD15+ granulocytes, CD14+ monocytes, CD8+ T cells, CD4+ T cells, CD19+ B cells, CD56+ NK cells, CD34+ HSCs, and/or non-blood cells such as from at least one of the cell type selected from endothelial cells, smooth muscle cells (aortic or intestine), and dermal fibroblasts.

In yet another preferred embodiment of the method according to the present invention, the sample is selected from a mammalian body fluid, including human blood samples, cord blood sample, or a tissue, organ or a sample of lymphocytes or a purified or separated fraction of such tissue, organ or lymphocytes or a cell type sample. Preferably, said mammal is a mouse, goat, dog, pig, cat, cow rat, monkey or human. The samples can be suitably pooled, if required. Preferably said cells are human cells, such as fetal cells.

Another preferred aspect of the method according to the present invention then further comprises the step of concluding on the immune and/or disease status of said mammal based on said EPCs. The EPCs can be quantified and be used as a benchmark to relatively quantify further detailed subpopulations, or it can be used as a predictive and/or screening and/or diagnostic and/or prognostic and/or adverse events detecting factor, or it can be used to finally detect this population to determine the overall immune or disease activity status.

In yet another preferred embodiment of the methods according to the present invention, the mammal suffers from or is likely to suffer from autoimmune diseases, transplant rejections, infection diseases, cancer, and/or allergy as but not limited to Trypanosoma cruzi-infection, Malaria and HIV infection; Hematologic Malignancies as but not limited to chronic Myelogenous Leukemia, Multiple Myeloma, Non Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, endometriosis, cardiovascular diseases, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of EPCs in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said EPCs as e.g. a sample for cell transfer into a patient.

Another preferred aspect of the method according to the present invention then relates to a method as above, further comprising formulating said EPCs as identified for transplantation into a patient. Pharmaceutical preparations for these purposes and methods for their production are performed according to methods known in the art of transplantation medicine.

Another preferred aspect of the method according to the present invention then further then relates to a method for treating a condition or disease in a mammal, in particular in a human, comprising a method according to the invention as above, and the step of transplanting EPCs as identified and isolated/multiplied in cell culture into a patient. Pharmaceutical preparations for these purposes and methods for their production are performed according to methods known in the art of transplantation medicine. The transplant can be autologous or allogenic.

Another preferred aspect of the method according to the present invention then further then relates to a method for treating and/or preventing a condition or disease in a mammal, in particular in a human, comprising a method according to the invention as above including a suitable treatment for said condition or disease comprising providing chemical and/or biological substances as above, and adjusting said treatment of the underlying disease or condition based on the results as provided by the method(s) of the invention. This may comprise the step of concluding on the immune or disease status of said mammal based on said EPCs. The EPCs can be quantified and be used as a benchmark to relatively quantify further detailed subpopulations, or it can be used as a predictive and/or screening and/or diagnostic and/or prognostic and/or adverse events detecting factor, or it can be used to finally detect this population to determine the overall immune activity status. This basis allows for adjusting said treatment, if necessary. Such adjustments may comprise the step of transplanting EPCs as identified and isolated/multiplied in cell culture into a patient as above, and/or providing additional chemical and/or biological substances for adjusting said treatment and/or prevention.

One particular example is a method for treating and/or preventing a condition or disease in a mammal, in particular in a human, wherein first a medicament is provided to said mammal. Respective medication strategies are known, optionally with suitable carriers and adjuvants. Therefore, the method then comprises measuring and/or monitoring the amount of EPCs in response to said medication that is/are provided to said mammal. In case of an insufficient number of EPCs, said treatment (here: medication) is adjusted, i.e. more drug is given. The method may be repeated until sufficient desired cells (i.e. a substantial population of EPCs) can be detected.

Treatment and/or prevention shall herein relate to the curing, prevention or alleviation of a disorder or malfunction of the body, i.e. bringing a body back to its healthy state.

Pharmaceutical preparations for these purposes and methods for their production are performed according to methods known in the art of a treatment using chemical and/or biological substances or transplantation medicine. Again, the transplant can be autologous or allogenic.

Another preferred aspect of the method according to the present invention relates to an oligomer according to any of SEQ ID No. 3 to 12, or an amplicon according to SEQ ID No. 2.

Yet another preferred aspect of the present invention then relates to a kit for identifying, quantifying, and/or monitoring EPCs in a mammal based on the analysis of the bisulfite accessibility of CpG positions in the genetic region for muscle myosin heavy chain 11/nuclear distribution protein nudE homolog 1 (MYH11/NDE1), comprising components for performing a method according to invention as described herein, in particular a kit comprising a) a bisulfite reagent, and b) materials for the analysis of the methylation status of CpG positions selected from the CpG positions in the region according to SEQ ID NO: 1 or 2, such as an oligomer selected from the sequences according to SEQ ID No. 3 to 12, or an amplicon as amplified by a primer pair based on SEQ ID No. 3 and 4 or 5 and 6 or 8 and 6 or 10 and 11 or a primer pair based on SEQ ID No. 3 and 4 or 5 and 6 or 8 and 6 or 10 and 11, respectively.

The present invention also encompasses the use of oligomers or amplicon or a kit according to the present invention for identifying and/or for monitoring EPCs in a mammal as described herein.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii)

bisulfite convertible (i.e. the "bisulfite convertibility") cytosine encompasses 5-formylcytosine (fC), 5-carboxycytosine (cC), as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

Biomarker Ration=$a/b$ $a=\Sigma$(C and/or mC and/or hmC and/or fC and/or cC)

$b=\Sigma$(C and/or mC and/or hmC and/or fC and/or cC), whereby a and b differ from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

In summary, using the MYH11/NDE1 genetic region and in particular the amplicon as described herein as a marker, the inventors very specifically identified, quantified and particularly differentiated EPCs, and in their relation to other cell types in a sample, for example to other blood cells.

The invention will now be further described in the following examples and with reference to the accompanying figures and the sequence listing, without being limited thereto. For the purposes of the present invention, all references as cited herein are incorporated by reference in their entireties.

FIG. 1 shows the analysis of CpG sites on amplicon AMP3968 (SEQ ID No. 2) according to the invention. The columns in the table correspond to the cell types as analyzed and the rows correspond to the CpG positions in the amplicon as analyzed (e.g. CpG 1, 2, etc.) with the positions indicated (AMP3968:67 corresponding to CpG at position 67 of Amplicon 3968 according to SEQ ID No. 2, . . . etc.).

FIG. 2 shows the genomic region surrounding the amplicon according to the present invention (SEQ ID No. 1, the amplicon sequence (SEQ ID NO. 2) is underlined.

FIG. 3 shows the genomic sequence of the amplicon according to the present invention (SEQ ID No. 2), the relevant CpG positions are bold and underlined.

Figure 1:
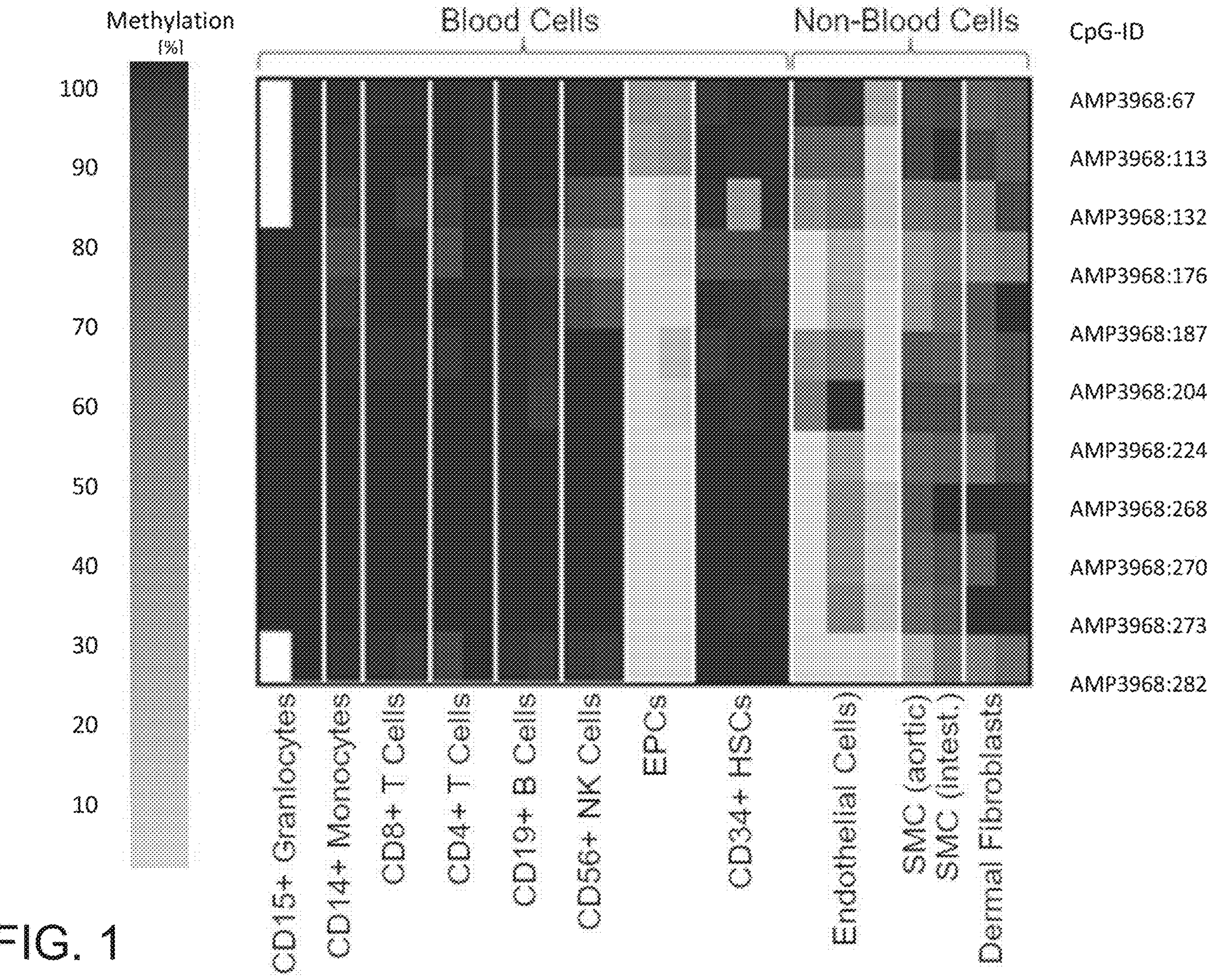

SEQ ID No. 1 shows the sequence of the MYH11/NDE1 genetic region surrounding the amplicon No. 3968 according to the present invention (see also FIG. 2).

SEQ ID No. 2 shows the genomic sequence of amplicon No. 3968.

SEQ ID Nos. 3 to 12 show the sequences of specific oligomers (primers and probes) according to the present invention.

EXAMPLES

Example 1

In order to identify EPCs, qPCR was performed on bisulphite converted samples stemming from the human genomic region according to the sequence SEQ ID No. 1 (see FIG. 2), in particular the region AMP3968 (underlined, and see FIG. 3).

For the actual epigenetic profiling of the amplicon region in blood cell subtypes, the immune cell populations as analyzed were as shown in FIG. 1.

The bisulfate-converted target-regions of preferred qPCR-assay-system as developed were:

```
Oligonucleotides for Bisulfite Sequencing (5'-3')
Forward Primer-
                                        (SEQ ID NO: 3)
GAAGGGTTTTGTGTGTATTTTT

Reverse Primer-
                                        (SEQ ID NO: 4)
AATTTTTCTTCCTTTCATACCA

Oligonucleotides of qPCR Assay (TpG Variant
i.e., demethylation-specific; 5'-3')-I
Forward Primer-
                                        (SEQ ID NO: 5)
CCCCAACATTTATCAAACATCAC

Reverse Primer-
                                        (SEQ ID NO: 6)
GGGTTATAAGTTAGAGATTATAAAGTTTATG

Probe-
                                        (SEQ ID NO: 7)
AAT+TACCA+CACCACAATTAC+CATAA*
*A plus sign in front of the letter indicates
that this is an LNA (locked nucleic acid)-based
nucleotide

Oligonucleotides of qPCR Assay (TpG Variant
i.e., demethylation-specific; 5'-3')-II
Forward Primer-
                                        (SEQ ID NO: 8)
ATCACAATAAACTCATTTCCTTCA

Reverse Primer-
                                        (SEQ ID NO: 6)
GGGTTATAAGTTAGAGATTATAAAGTTTATG
```

-continued

Probe- (SEQ ID NO: 9)

AACTAA+TTACCACAC+CACAAT+TACC*

*A plus sign in front of the letter indicates that this is an LNA (locked nucleic acid)-based nucleotide Oligonucleotides of qPCR Assay (CpG Variant i.e., methylation-specific; 5'-3')

Forward Primer- (SEQ ID NO: 10)

CCCGACATTTATCAAACATCG

Reverse Primer- (SEQ ID NO: 11)

GGTTATAAGTTAGAGATTATAAAGTTTACG

Probe- (SEQ ID NO: 12)

TTACCGCGCCGCAATTACCGT

The analysis of the demethylation status of purified (immune) cell preparations with the EPC qPCR assay (TpG PU/GAPDH PU) was found to be as follows (Table 1):

| Cell type | Description | Demethylation (%) |
|---|---|---|
| EPC (cord blood) - sample 1 | CD31 > 50%, vWF > 50%, CD105 > 50%, CD34 > 34%, Ac-LDL > 50% | 93.7 |
| EPC (cord blood) - sample 2 | CD31 > 50%, vWF > 50%, CD105 > 50%, CD34 > 34%, Ac-LDL > 50% | 91.4 |
| EPC (cord blood) - sample 3 | CD31 > 50%, vWF > 50%, CD105 > 50%, CD34 > 34%, Ac-LDL > 50% | 103.00 |
| Endothelial cells | vWB+; CD31+; CD146+; CD105+ | 42.4 |
| Endothelial cells | vWB+; CD31+; CD146+; CD105+ | 30.6 |
| HSC (CD34+ stem cells) | CD34+ | 0.0 |
| HSC (CD34+ stem cells) | CD34+ | 0.0 |
| Fibroblasts | — | 5.2 |
| Fibroblasts | — | 0.0 |
| Smooth muscle cells | Alpha-smooth muscle actin | 21.5 |
| Smooth muscle cells | Alpha-smooth muscle actin | 16.6 |
| T Helper cells | CD3+/CD4+/CD8− | 0.0 |
| T Helper cells | CD3+/CD4+/CD8− | 0.0 |
| Cytotoxic T cells | CD3+/CD8+/CD4− | 0.0 |
| Cytotoxic T cells | CD3+/CD8+/CD4− | 0.0 |
| B cells | CD19+/IgG−/CD3−/CD27+/CD14−/CD11c−/CD16−/CD56− | 4.0 |
| NK cells | CD3−/CD56+/CD16+ | 0.0 |
| Monocytes | CD14+ | 0.0 |
| Granulocytes | CD15++ | 0.0 |

The invention claimed is:

1. A method for producing an amplicon, the method comprising a) bisulfite treating isolated genomic DNA from a mammalian cell sample to generate bisulfite treated DNA, and b) producing the amplicon by amplifying from the bisulfite treated DNA a region of muscle myosin heavy chain 11/nuclear distribution protein nudE homolog 1 (MYH11/NDE1) comprising SEQ ID NO: 2 prior to bisulfite treatment, wherein at least the cytosine-phosphate-guanine (CpG) at position 268 in the region of SEQ ID NO: 2 comprises bisulfite convertible cytosine.

2. The method according to claim 1, further comprising a bisulfite convertible cytosine at at least one CpG position selected from the CpG positions 270 and 273 in the region of SEQ ID NO: 2.

3. The method according to claim 1, wherein the bisulfite convertible cytosine is detected by a method selected from a methylation specific enzymatic digest, bisulfite sequencing, promoter methylation analysis, CpG island methylation analysis, MSP, and other methods relying on a detection of amplified DNA.

4. The method according to claim 1, wherein said sample is selected from a mammalian body fluid, a cord blood sample or a fraction thereof, a tissue, an organ, or a blood sample or a fraction thereof.

5. The method according to claim 1, wherein said method is performed without a step of purifying and/or enriching said cell sample.

6. The method according to claim 1, wherein said cell sample is from a mammal that suffers from or is likely to suffer from autoimmune diseases, transplant rejections, infection diseases, cancer, endometriosis, cardiovascular diseases, and/or allergy.

7. The method of claim 1, wherein the method is performed using a kit comprising an oligomer according to any of SEQ ID NOs: 3 to 12, the amplicon comprising SEQ ID NO: 2, or the bisulfite treated sequences thereof.

8. The method of claim 1, further comprising a bisulfite convertible cytosine at at least one CpG position selected from CpG positions 67, 113, 132, 176, 187, 204, 224, 270, 273, and 282 of SEQ ID NO: 2.

9. The method of claim 1, wherein said mammalian cell sample is from a human.

10. The method of claim 7, wherein the kit further comprises a bisulfite reagent.

11. The method according to claim 1, wherein the mammalian cell sample is whole blood and/or non-trypsinzed tissue.

* * * * *

SEQUENCE LISTING

```
<160> NUMBER OF SEQ ID NOS: 12

<210> SEQ ID NO 1
<211> LENGTH: 1083
<212> TYPE: DNA
<213> ORGANISM: Homo sapiens

<400> SEQUENCE: 1

gcgccattgc actccagagc gagactccgt ctcaaaaaaa aaaaaaaaaa aaagcaaaat      60

cccagagcag cagagacctc ttcatgcttt cttgggaagg gccctgtgtg catccttgag     120

tcttgggtat ccactcccca gtccctgaac atgtacatgc ccgtgaagcc tccagaaaag     180

gctctgccag gactgtgctt ggctttgcgg tggtcagctt ccaccccgtg tgctgaaaat     240

gcagtttgta gctagacatc actcaagcca cgtgcagccc ccggcatttg tcagacatcg     300

cagtgagctc atttccttcg cagacaagcc tgtgaaagct gaatcatggg aggactggtt     360

gccgcgccgc agttaccgtg aactttgtga tctctgactt gtgacccaga ccagccaact     420

agaagccaag tacgttctcc aggaatgtgc ccagatagtg gaactgtcat attcattcag     480

tgcagtgtct tcactggaca agggaggaca gcactgctga gtgccctaac cacgtaagag     540

tggcttttgg catgaaagga agaaaaatcc aagctacaca cacagcctct gccatctcgt     600

caagatgcag tgataagggc gcacactgtt gggtgtcatg tcacatgtgc tgcccagagg     660

caggaaggac agtgggtcaa gagatgaggt ctatttgtca tcctgatctt ggtttcaatg     720

aaagctttgc acaaagatat ccaagcctcc agattttgca agaatctcgt ggaaatgtgc     780

aagggtttaa aaattggggt gggcagaggg gcgcattggg cagaaaagaa atggatactg     840

agacaacaca cagctgcgaa gctgaaggca tgatacctgg tgcatcactg cgaagtttcc     900

tgtggggggg gccctctgaa acagagagag aatccccgga ggttaccatc agcaaacaag     960
```

```
aaggagcccg gttaagtata ttcttaattg ttaaagacat ttgcttcgat ttaataatta   1020

aaggcactct tttttatttt gagatagtct ctgtcaccca ggctggagtg caggggtgcg   1080

atc                                                                 1083


<210> SEQ ID NO 2
<211> LENGTH: 474
<212> TYPE: DNA
<213> ORGANISM: Homo sapiens

<400> SEQUENCE: 2

gaagggccct gtgtgcatcc ttgagtcttg ggtatccact ccccagtccc tgaacatgta     60

catgcccgtg aagcctccag aaaaggctct gccaggactg tgcttggctt tgcggtggtc    120

agcttccacc ccgtgtgctg aaaatgcagt ttgtagctag acatcactca agccacgtgc    180

agcccccggc atttgtcaga catcgcagtg agctcatttc cttcgcagac aagcctgtga    240

aagctgaatc atgggaggac tggttgccgc gccgcagtta ccgtgaactt tgtgatctct    300

gacttgtgac ccagaccagc caactagaag ccaagtacgt tctccaggaa tgtgcccaga    360

tagtggaact gtcatattca ttcagtgcag tgtcttcact ggacaaggga ggacagcact    420

gctgagtgcc ctaaccacgt aagagtggct tttggcatga aaggaagaaa aatc          474


<210> SEQ ID NO 3
<211> LENGTH: 22
<212> TYPE: DNA
<213> ORGANISM: Homo sapiens

<400> SEQUENCE: 3

gaagggtttt gtgtgtattt tt                                              22


<210> SEQ ID NO 4
<211> LENGTH: 22
<212> TYPE: DNA
<213> ORGANISM: Homo sapiens

<400> SEQUENCE: 4

aatttttctt cctttcatac ca                                              22


<210> SEQ ID NO 5
<211> LENGTH: 23
<212> TYPE: DNA
<213> ORGANISM: Homo sapiens

<400> SEQUENCE: 5

ccccaacatt tatcaaacat cac                                             23


<210> SEQ ID NO 6
<211> LENGTH: 31
<212> TYPE: DNA
<213> ORGANISM: Homo sapiens

<400> SEQUENCE: 6

gggttataag ttagagatta taaagtttat g                                    31


<210> SEQ ID NO 7
<211> LENGTH: 25
<212> TYPE: DNA
<213> ORGANISM: Homo sapiens

<400> SEQUENCE: 7

aattaccaca ccacaattac cataa                                           25
```

-continued

```
<210> SEQ ID NO 8
<211> LENGTH: 24
<212> TYPE: DNA
<213> ORGANISM: Homo sapiens

<400> SEQUENCE: 8

atcacaataa actcatttcc ttca                                              24


<210> SEQ ID NO 9
<211> LENGTH: 25
<212> TYPE: DNA
<213> ORGANISM: Homo sapiens

<400> SEQUENCE: 9

aactaattac cacaccacaa ttacc                                             25


<210> SEQ ID NO 10
<211> LENGTH: 21
<212> TYPE: DNA
<213> ORGANISM: Homo sapiens

<400> SEQUENCE: 10

cccgacattt atcaaacatc g                                                 21


<210> SEQ ID NO 11
<211> LENGTH: 30
<212> TYPE: DNA
<213> ORGANISM: Homo sapiens

<400> SEQUENCE: 11

ggttataagt tagagattat aaagtttacg                                        30


<210> SEQ ID NO 12
<211> LENGTH: 21
<212> TYPE: DNA
<213> ORGANISM: Homo sapiens

<400> SEQUENCE: 12

ttaccgcgcc gcaattaccg t                                                 21
```